(12) United States Patent
Dambrowsky et al.

(10) Patent No.: US 8,231,928 B2
(45) Date of Patent: Jul. 31, 2012

(54) METHOD FOR PRODUCING A LAYER ON A MOLDED ARTICLE AND USE THEREOF

(75) Inventors: Nina Dambrowsky, Berlin (DE); Stefan Giselbrecht, Karlsruhe (DE); Roman Truckenmueller, Flein (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 649 days.

(21) Appl. No.: 12/279,817

(22) PCT Filed: Feb. 2, 2007

(86) PCT No.: PCT/EP2007/000892
§ 371 (c)(1),
(2), (4) Date: Aug. 21, 2009

(87) PCT Pub. No.: WO2007/093290
PCT Pub. Date: Aug. 23, 2007

(65) Prior Publication Data
US 2009/0317853 A1    Dec. 24, 2009

(30) Foreign Application Priority Data

Feb. 17, 2006   (DE) .................. 10 2006 007 397

(51) Int. Cl.
*G01N 1/28* (2006.01)
(52) U.S. Cl. ....... 427/2.11; 205/126; 427/304; 427/305; 427/301; 427/58; 427/553; 428/323
(58) Field of Classification Search .......... 427/2.11, 427/304, 305, 301, 58, 553; 205/126; 428/323
See application file for complete search history.

(56) References Cited

U.S. PATENT DOCUMENTS

| | | | |
|---|---|---|---|
| 4,661,384 A * | 4/1987 | Sirinyan et al. | 427/304 |
| 5,525,205 A * | 6/1996 | Miyashita | 205/126 |
| 7,060,421 B2 | 6/2006 | Naundorf et al. | |
| 2004/0026254 A1 | 2/2004 | Hupe et al. | |

FOREIGN PATENT DOCUMENTS

| | | |
|---|---|---|
| EP | 0641152 | 3/1995 |
| EP | 1191127 | 3/2002 |
| EP | 1274288 | 1/2003 |

OTHER PUBLICATIONS

Kordas et al., Palladium thin film deposition of polyimide by CW Ar+ laser radiation for electroless copper plating, Thin Solid Films, 384, (2001), pp. 185-188.*
Stransky, Reinhard: "New 3-D-MID process set to boost mechatronic applications Ultramid T as carrier for electrical circuits: MID and laser direct structuring"; BASF News Release: TRade Press Conference K 2004, (online), Jun. 22, 2004-Jun. 23, 2004 XP002449662.
Krautheim, T.B. "Production Methods, Usage Requirements and Material Parameters of Three-Dimensional Electronic Modules, 3-D MID", Manual for Users and Manufacturers, Research Association for Three-Dimensional Eklectronic Modules, 2nd edition, 1999.
Shafeev, G.A. et al. "Light Enhanced Electroless Cu Deposition on Laser-Treated Polyimide Surface", Appl Surface Sci. 138-139, 455-460 (1999).
Kordas, K. et al. "Thin Film Deposition on Polyimide by Cw Ar+ Laser Radiation for Electroless Copper Plating", Thin Solid Films 384, 185-188 (2001).
Cicoira, F. et al. "Auger Electron Spectroscopy Analysis of High Metal Content Microstructures Grown by Electron Beam Induced Deposition", Appl. Surface Sci. 242, 107-113 (2005).
Utke, I. et al."Electron Beam Induced Deposition of Metallic Tips and Wires for Microelectronics Applications", Microelectr, Engineering 53, 261-264 (2000).

* cited by examiner

*Primary Examiner* — Dah-Wei Yuan
*Assistant Examiner* — Andrew Bowman
(74) *Attorney, Agent, or Firm* — Leydig, Voit & Mayer, Ltd.

(57) ABSTRACT

A method for producing a layer on a molded article. The method includes providing a formable film. Galvanically catalytically active nuclei are anchored to at least one region of the formable film provided for the layer. The formable film is shaped so as to form the molded article. A galvanic deposition is performed on a surface of the molded article so as to bond the nuclei to form the layer.

13 Claims, No Drawings

METHOD FOR PRODUCING A LAYER ON A MOLDED ARTICLE AND USE THEREOF

CROSS REFERENCE TO PRIOR APPLICATIONS

This application is a U.S. National Phase application under 35 U.S.C. §371 of International Application No. PCT/EP2007/000892, filed on Feb. 2, 2007 and claims benefit to German Patent Application No. DE 10 2006 007 397.5, filed on Feb. 17, 2006. The International Application was published in German on Aug. 23, 2007 as WO 2007/093290 A2 under PCT Article 21(2) present.

FIELD

The present invention relates to a method for producing an electrically conductive layer on a molded article that is formed by shaping a film.

BACKGROUND

Besides injection molding, the hot forming or thermoforming of thin thermoplastic films and plates, which are fixedly clamped at the edges, into three-dimensional molded articles, accompanied by thinning of the wall thicknesses thereof, constitutes the most important method in the macroscopic range for manufacturing large numbers of plastic articles. In contrast to injection molding, this method makes it possible to produce thin-walled, large-area, three-dimensional microstructured parts and microstructures in the microtechnical range.

Conductor tracks on three-dimensional injection-molded or hot-stamped plastic parts are mostly fabricated using MID technology (molded interconnect devices). Typical variants of this method include, for example, two-component injection molding, hot-stamping, mask-exposure methods, laser direct structuring and film insert molding. Known methods can be used to produce three-dimensional structures having integrated conductor tracks. Such methods do not, however, lend themselves to the fabrication of three-dimensional, membrane-type structures that are thin-walled on all sides, particularly not to those having undercuts.

When the existing MID method is employed, the problem arises that conductor tracks can only be introduced into three-dimensional structures at great outlay and/or at widths greater than 10 μm. This limits the design freedom, particularly when working with structures on the microscopic scale.

In this context, among the MID methods, two-component injection molding offers the greatest geometric freedom. However, depending on the flow properties and the flow lengths in the tool, the smallest feasible conductor track width is within a size range of about 250 μm. See Krautheim, T. B., *Herstellungsverfahren, Gebrauchsanforderungen und Materialkennwerte Räumlicher Elektronischer Baugruppen 3-D MID* [Production Methods, Usage Requirements and Material Parameters of Three-Dimensional Electronic Modules, 3-D MID]: Manual for Users and Manufacturers, Research Association for Three-Dimensional Electronic Modules, 2nd edition, 1999.

It may be that smaller conductor track geometries (of approximately 125 μm) are attainable using other methods, such as, for example, hot-stamping. However, they pose clear limitations on the design of the molded articles. In the case of laser structuring, geometries of up to approximately 30 μm are partially attainable (for example, using semi-additive methods). However, in this case, complex component geometries require substantial systems engineering work (multi-axis systems, 3D focal position control).

The disadvantage typically associated with resist-based laser structuring methods is that it is only possible to homogeneously coat three-dimensional components when working with comparatively simple geometries. This method is therefore only economical on a large scale in the area of fine conductor structuring. See Krautheim, cited above.

Mask-based methods for the laser structuring of conductor tracks either have the disadvantages typical of a mask projection, or they necessitate the fabrication of costly three-dimensional masks for the exposure process. Therefore, the contact masking method is also only suited for relatively simple component geometries and for relatively large components since, in the microscopic range, considerable additional outlay is still required for precise positioning. In the case of film insert molding, the three-dimensionality of the structures is limited due to the occurrence of folds during the shaping process.

SUMMARY

It is an aspect of the present invention to provide a method for producing a layer on a molded article that is preferably electrically conductive and which therefore may be used for applying very narrow conductor tracks or electrodes to three-dimensional, thin-walled microstructures.

In an embodiment, the present invention provides for a method for producing a layer on a molded article. The method includes providing a formable film. Galvanically catalytically active nuclei are anchored to at least one region of the formable film provided for the layer. The formable film is shaped so as to form the molded article. A galvanic deposition is performed on a surface of the molded article so as to bond the nuclei to form the layer.

DETAILED DESCRIPTION

A formable film can be prepared, of, for example, plastic such as a thermoplastic plastic. Examples include polymethyl methacrylate PMMA, polyethylene PE, polypropylene PP, polycarbonate PC, polystyrene PS, polyamide PA, polyethylene terephthalate PET, polyimide PI, polyvinyl(idene) chloride PV(D)C, polyvinyl(idene) fluoride PV(D)F or cycloolefincopolymer (COC). The film, which may be two- or multilayered, preferably can have a thickness of 1 to 1000 μm, for example, 5 to 200 μm or 20 to 50 μm.

The surface of the prepared plastic is subsequently activated in accordance with step b) in selected (sub)regions. To that end, a method is utilized that makes it possible for galvanically catalytically active nuclei to be deposited or produced in a punctiform manner (locally) in the selected regions.

Methods, which can be used for this purpose, employ light or particle radiation, such as PVD/CVD processes, laser or electron beam-enhanced methods or raster patterning methods. See Shafeev, G. A. & Hoffmann, P., *Light Enhanced Electroless Cu Deposition on Laser-Treated Polyimide Surface*, Appl. Surface Sci. 138-139, 455-460 (1999); Kordas, K., Leppavuori, S., Uusimaki, A., George, T. F., Nanai, L., Vajtai, R., Bali, K. & Bekesi, J., Palladium *Thin Film Deposition on Polyimide by CW Ar+ Laser Radiation for Electroless Copper Plating*, Thin Solid Films 384, 185-188 (2001); Cicoira, F., Hoffmann, P., Olsson, C. O. A., Xanthopoulos, N., Mathieu, H. J. & Doppelt, P., *Auger Electron Spectroscopy Analysis of High Metal Content Microstructures Grown by Electron Beam Induced Deposition*, Appl. Surface Sci. 242, 107-113 (2005); and Utke, I., Dwir, B., Leifer, K., Cicoira, F., Doppelt, P., Hoffmann, P. & Kapon, E., *Electron Beam Induced Deposition of Metallic Tips and Wires for Microelectronics Applications*, Microelectr. Engineering 53, 261-264 (2000). Since the starting material, a formable film, can be a planar substrate, a high-resolution and simple direct structuring or, alternatively, a mask-based structuring may be carried out.

The film provided with nuclei (nucleated) in selected (sub) regions can be shaped, for example stretched in a forming process such as a thermoforming process, into a three-dimensional molded article. However, since the film maintains its material cohesion during and following this process step and, at most, is stretched in a rubber-elastic phase, the structure of the activated surfaces can be retained, even if distorted in response to the stretching.

The production of a closed layer already on the film may, in contrast, fail in response to stretching, particularly if it is a question of a metallic layer that tends to form cracks to a much greater degree than does the film. In such a case, cracks may form which could potentially be so extensive that electroless galvanization may no longer be able to bridge or close them.

If, however, as in the method according to the present invention, only individual galvanically catalytically active nuclei are produced on the surface of the film or are applied to the surface of the film, then the areal density of the nuclei may change in response to the stretching of the film.

The type of modification to the surface of the film may be selected so that the galvanically catalytically active nuclei do not lose their catalytic properties during the shaping process. Suited for this, in particular, are atoms, molecules, clusters or metallic particles, such as of noble metals, which either remain physically adhered to the surface or covalently bonded thereto.

The molded article produced can then be brought into contact with an electroless electrolyte, whereby the galvanically catalytically active nuclei form a closed metallic layer over the surface area, which may be electrically conductive, in each case within the desired regions. For the electroless deposition, depending on the application, metals known from galvanization processes, such as nickel, copper, gold, platinum or palladium are suited. When selecting the metal to be deposited, the catalytic properties of the nuclei should be properly tuned to the electrolyte, to render possible deposition and layer formation.

The method according to the present invention provides advantages over the known MID methods. A structuring at a substantially higher resolution than existing methods is made possible by the process of prestructuring on a film.

A further advantage resides in that the geometry of the molded article is essentially limited only by the thermoforming process itself, but not by the structuring of the conductor tracks. Therefore, even given pronounced stretching, it is possible to provide complex three-dimensional microstructures with conductor tracks, as long as the structure itself is able to be produced using a thermoforming process. The method according to the present invention makes it possible for three-dimensional microstructures that are thin-walled on all sides to be provided with conductor tracks.

Particularly in applications where conductor tracks fabricated using the method according to the present invention are intended to be used as heating elements or for coupling electromagnetic fields into or out of the microstructure, it is advantageous when this only needs to be effected through extremely thin films. Thus, the contents of a thermoformed microcavity used, for example, for storing inorganic or organic molecules, biomolecules, prokaryotic or eukaryotic cells or tissues, or as a cell container for cultivating or expanding prokaryotic or eukaryotic cells, or as a biosensor or bioreactor, may be heated more quickly by a heating conductor located on the outer surface, while expending relatively little energy, since the heat-insulating plastic film is extremely thin in this region.

The present invention is explained in greater detail in the following with reference to an exemplary embodiment.

To this end, a 50 µm thick polycarbonate film having a single-sided statistical surface roughness was prepared as a substrate. On the roughened side of the film, gold nuclei were anchored by PVD (physical vapor desposition) using a slit diaphragm (slit width approximately 50 µm) onto the desired regions on the surface of the film (nucleation of the film).

The (nucleated) film provided with nuclei in the region of the slit is thermoformed into a three-dimensional molded article, the rough and partially activated surface forming the inner surface of the molded article. To this end, cylindrical microcavities having diameters of 350 µm of a mold tool were molded into the film at a depth of 150 µm. In response to the stretching process, the wall thickness was thinned out, becoming partially substantially less than 50 µm thick.

The molded article, which had been nucleated in partial regions on the surface thereof, was subsequently placed entirely in an electroless autocatalytic gold electrolyte, care having been taken to ensure a complete wetting of the surface. Following removal, the molded article was rinsed and dried. An uninterrupted electric conductivity was able to be established over a plurality of microcavities. The width of the conductor track was approximately 80 µm; its length approximately 20 mm.

The invention claimed is:

1. A method for producing a layer on a molded article, comprising:
   providing a plastic formable film wherein the formable film includes a plastic;
   providing galvanically catalytically active nuclei anchored to at least one region of the formable film provided for the layer;
   shaping the formable film so as to form the molded article; and
   performing a galvanic deposition on a surface of the molded article so as to bond the nuclei to form the layer, wherein the shaping includes at least one of thermoforming and deep-drawing.

2. The method as recited in claim 1, wherein at least one of individual atoms, molecules, clusters and particles are used as the galvanically catalytically active nuclei.

3. The method as recited in claim 1, wherein the galvanically catalytically active nuclei have metallically conductive properties.

4. The method as recited in claim 1, wherein the galvanically catalytically active nuclei include a noble metal.

5. The method as recited in claim 1, wherein the galvanically catalytically active nuclei include an organometallic compound.

6. The method as recited in claim 1, wherein the galvanically catalytically active nuclei have at least one of autocatalytic, ionogenic and colloidal properties.

7. The method as recited in claim 1, wherein a galvanic deposition is performed by generating the nuclei on the surface by at least one of light and particle radiation.

8. The method as recited in claim 1, wherein the plastic is a thermoplastic plastic.

9. The method as recited in claim 1, wherein the shaping includes heating the formable film.

10. The method as recited in claim 1, wherein the formable film has a thickness of 1 μm to 1000 μm.

11. The method as recited in claim 1, wherein the performing the galvanic deposition includes galvanically depositing at least one of nickel, copper, gold, platinum and palladium on the surface.

12. The method as recited in claim 1, further comprising activating the formable film.

13. The method as recited in claim 1, further comprising contacting the molded article with an electroless electrolyte.

* * * * *